US00PP19266P2

(12) United States Plant Patent
Stephens

(10) Patent No.: US PP19,266 P2
(45) Date of Patent: Sep. 23, 2008

(54) ***ILEX* PLANT NAMED 'CAROLINA RUBY'**

(50) Latin Name: *Ilex vomitoria*
Varietal Denomination: Carolina Ruby

(76) Inventor: Carroll T. Stephens, 22 Stephens Estate, North Augusta, SC (US) 29860

( * ) Notice: Subject to any disclaimer, the term of this patent is extended or adjusted under 35 U.S.C. 154(b) by 271 days.

(21) Appl. No.: 11/325,195

(22) Filed: Jan. 3, 2006

(51) Int. Cl.
*A01H 5/00* (2006.01)

(52) U.S. Cl. ..... Plt./226
(58) Field of Classification Search ..... Plt./226, Plt./247
See application file for complete search history.

*Primary Examiner*—Kent L. Bell
*Assistant Examiner*—Georgia Helmer

(57) ABSTRACT

A new female cultivar of *Ilex vomitoria* named 'CAROLINA RUBY' that is characterized by its dwarf stature and compact habit and its prolific and abundant fruiting when pollinated by an appropriate male form of the species. In combination these traits set 'CAROLINA RUBY' apart from all other existing varieties of *Ilex vomitoria* known to the inventor.

3 Drawing Sheets

Genus: *Ilex.*
Species: *vomitoria.*
Denomination: 'CAROLINA RUBY'.

BACKGROUND OF THE INVENTION

The present invention relates to a new and distinct cultivar of *Ilex vomitoria,* commonly known as Yaupon Holly, and widely grown in the south-eastern United States an ornamental evergreen flowering shrub which, if the variety is female, will bear bright red fruits in the fall and persisting throughout the winter.

The new cultivar is known botanically as *Ilex vomitoria* and will be referred to hereinafter by the cultivar name 'CAROLINA RUBY'.

'CAROLINA RUBY' is principally grown for its fruit. In the conditions of USDA Zone 8, 'CAROLINA RUBY' begins to flower in early April and will continue in flower for two to three weeks. Since the species *Ilex vomitoria* is dioecious, and since 'CAROLINA RUBY' is female, an appropriate male pollinator is necessary. The male variety *Ilex vomitoria* 'Schillings' (unpatented) is an ideal pollinator since it is widely distributed in cultivation and also flowers at the same time as 'CAROLINA RUBY'.

'CAROLINA RUBY' arose and was selected by the inventor at the inventor's nursery in North Augusta, S.C. as a single seedling of *Ilex vomitoria* 'Folsom's Weeping' (unpatented). *Ilex vomitoria* 'Folsom's Weeping' is a large growing variety, typically achieving a height of 4 to 5 meters, and also exhibiting a cascading or weeping plant habit. Seed of *Ilex vomitoria* 'Folsom's Weeping' was sown by the inventor in 1986. After two years germination period, as is typical of the species *Ilex vomitoria,* the inventor observed seedling emergence in 1988. The inventor observed the growth of all the seedlings and found that all seedlings except one developed at a growth rate which was typical of the parent, *Ilex vomitoria* 'Folsom's Weeping'. This one particular seedling, the present invention 'CAROLINA RUBY', remained very small in comparison with all of its siblings by virtue of an annual growth rate of approximately 20% of the growth rate of its parent. By 1995, when 'CAROLINA RUBY' was approximately seven years old from germination, its height was approximately 70 cm in height whereas its siblings had achieved a height of approximately 3 meters.

Although 'CAROLINA RUBY' was of interest to the inventor due to its exceptional dwarfness, the inventor considered that its commercial potential would be significantly greater if 'CAROLINA RUBY' were to bear female flowers and therefore carry berries. 'CAROLINA RUBY' first flowered in 1995, at seven years of age, and the inventor observed that berries were formed in the fall of that year. In subsequent years, the inventor observed that the berry set was approximately five times more prolific than the typical berry set of the species, or the parent, or any of the sibling seedlings of 'CAROLINA RUBY'. Moreover, the inventor observed that the berries of 'CAROLINA RUBY' completely encircled the branches to the degree that portions of the stems became completely hidden. In further observation, as the inventor grew more plants of 'CAROLINA RUBY', flowering and fruiting were found to occur on two and three year old wood, so that berries are carried on older portions of stems which have completely shed their leaves.

The first asexual reproduction of 'CAROLINA RUBY' was conducted by the inventor in 1996 at the inventor's nursery in North Augusta, S.C. The method used for asexual propagation was semi-hardwood cuttings. The inventor grew off these first cuttings and determined that the characteristics of 'CAROLINA RUBY' were stable and were reproduced true to type. The inventor has since determined that 'CAROLINA RUBY' reproduces true to type in all successive generations of asexual reproduction.

SUMMARY OF THE INVENTION

The following traits have been repeatedly observed and represent the characteristics of 'CAROLINA RUBY'. These traits in combination distinguish 'CAROLINA RUBY' from all other varieties of *Ilex vomitoria* known to the inventor. 'CAROLINA RUBY' has not been tested under all possible conditions and phenotypic differences may be observed with variations in environmental, climatic and cultural conditions, without however, any difference in genotype.

1. 'CAROLINA RUBY' is a dwarf form of its species since it grows to a height not exceeding 1.0 meter in seven years from a rooted cutting.
2. 'CAROLINA RUBY' is a female form of its species and bears bright red globular berries in profusion from fall and persisting through winter if an appropriate male pollinator is present in the vicinity.

BRIEF DESCRIPTION OF THE DRAWINGS

The accompanying two color drawings illustrate the overall appearance of the new cultivar 'CAROLINA RUBY' showing the colors as true as it is reasonably possible to obtain in colored reproductions of this type. Colors in the photographs may differ from the color values cited in the detailed botanical description, which accurately describe the actual colors of the new variety of 'CAROLINA RUBY'.

The drawing labeled as FIG. 1 illustrates a plant of 'CAROLINA RUBY' which is seven years old from a rooted cutting and is established in the ground at the inventor's nursery in North Augusta, S.C.

Figure 1:
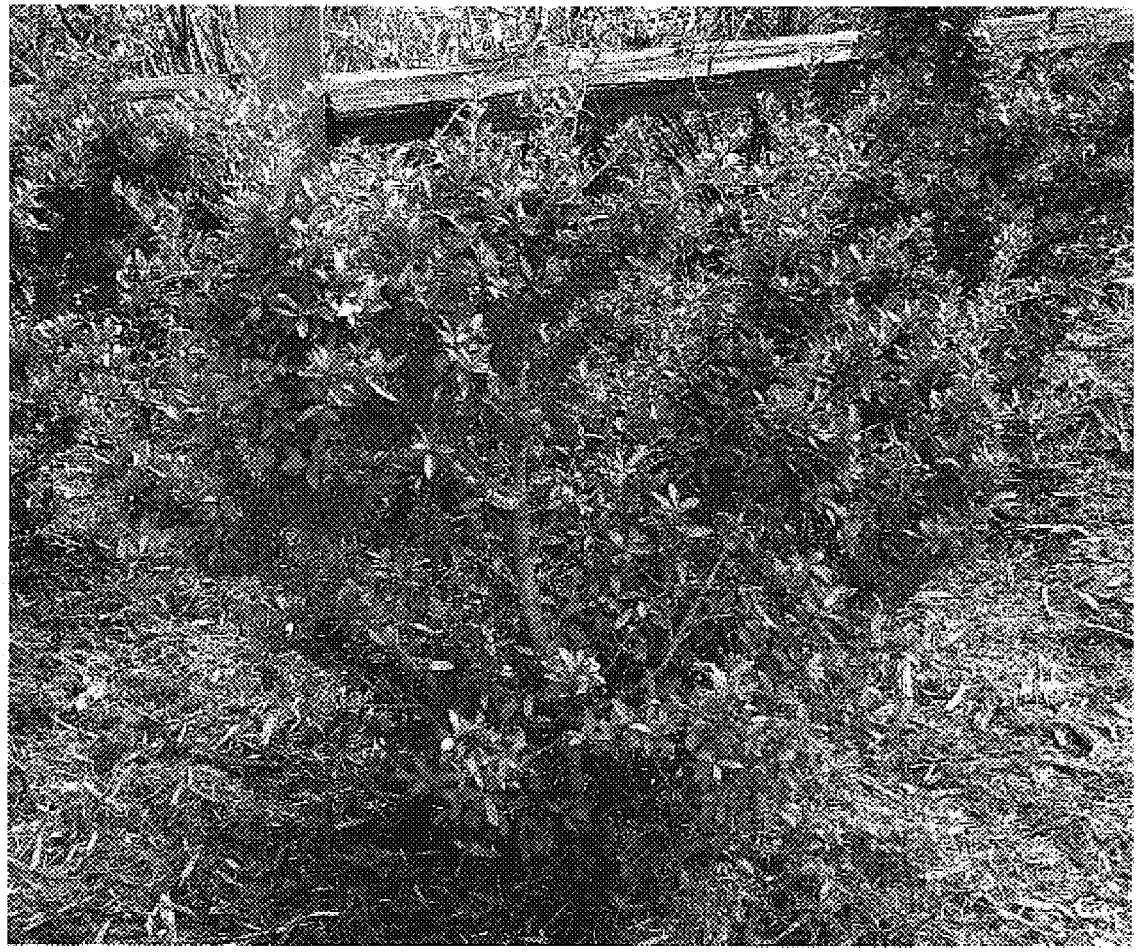
Figure 2:
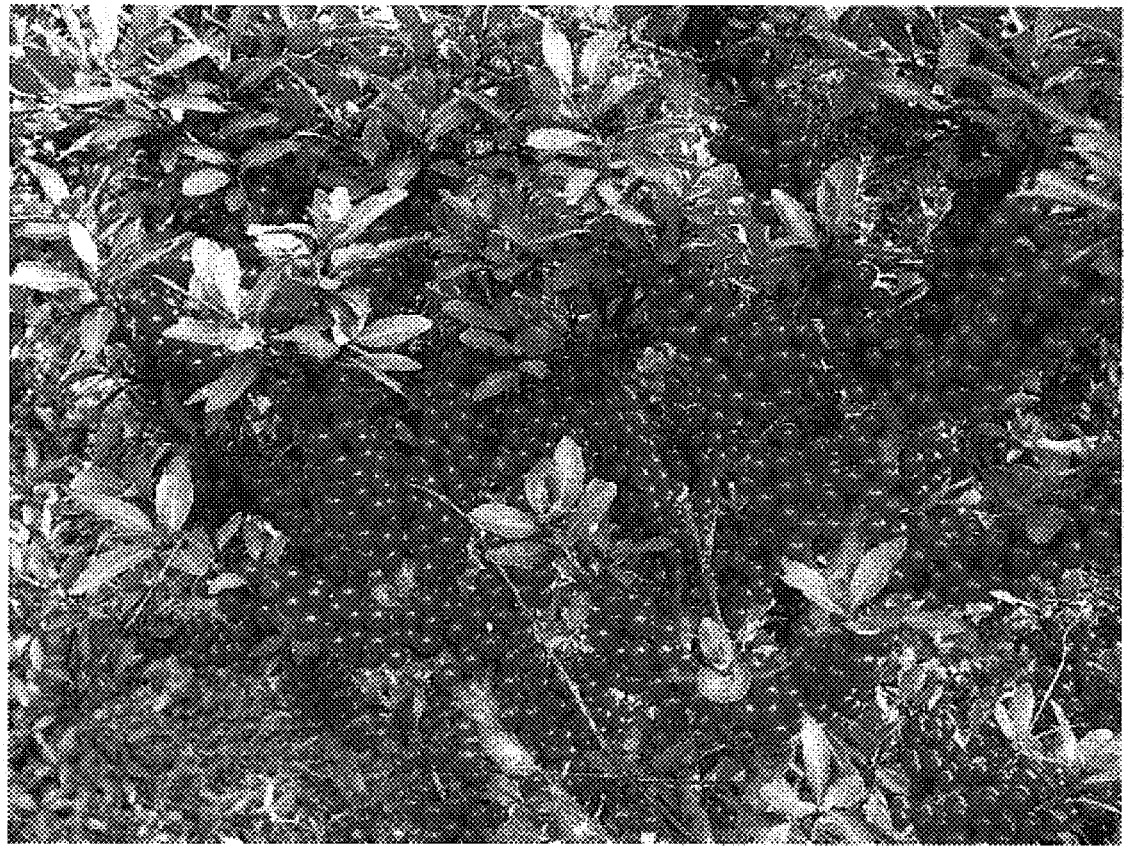

The drawing labeled as FIG. 2 illustrates a close-up view of the clusters and fruits of 'CAROLINA RUBY'.

Figure 3:
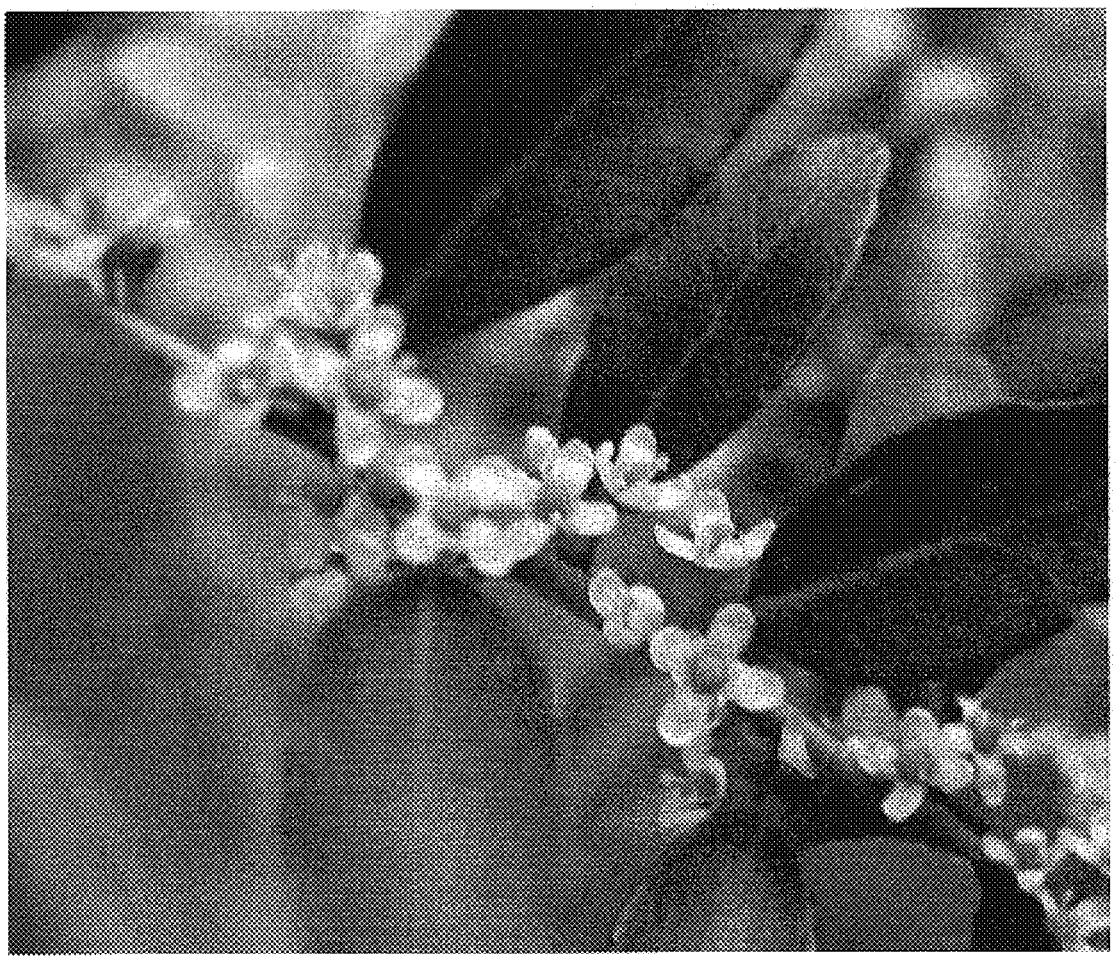

The drawing labeled as FIG. 3 illustrates the flowers of 'CAROLINA RUBY'.

BOTANICAL DESCRIPTION OF THE PLANT

The following is a detailed description of 'CAROLINA RUBY'. Botanical data was collected during the 2005 growing season from plants which were approximately seven years old from a rooted cutting. The observed plants were growing out of doors in the ground in North Augusta, S.C. The observed plants had not been pinched or pruned and had flowered and fruited naturally. The color determinations have been made by reference to the 2001 edition of The Royal Horticultural Society Colour Chart, except where general color terms of ordinary dictionary significance are used.

Family: Aquifoliaceae.
Botanical classification: *Ilex vomitoria.*
Genus: *Ilex.*
Species: *vomitoria.*
Variety denomination: 'CAROLINA RUBY'.
Common name: Yaupon Holly.
Use: Ornamental shrub.
Container size: Suggested container sizes for planting: 1, 3, 5 or 7 gallon.
Cultural requirements: Similar to the species, including a preference for planting in well drained soil with pH in range from 5 to 7.
Light requirement: Fruiting is most prolific when grown in good light, either full or partial sun, but not in full shade.
Pollination requirements: Requires a male pollinator in the vicinity, generally within 30 meters distance, as bees act as pollinators. The dwarf male variety *Ilex vomitoria* 'Schillings' (unpatented) makes an ideal pollinator.
Parentage: A chance seedling of *Ilex vomitoria* 'Folsom's Weeping' (unpatented).
Plant description:
- *Bloom period.*—Flowers start to open in early April and continue for two to three weeks.
- *Sexuality.*—Female.
- *Plant habit.*—Shrubby, twiggy, more compact than the species.
- *Vigor.*—Although compact and slower-growing than the species, approximately 10 cm to 15 cm of new growth takes place each season. If pollinating male plants are present, fruit is set and growth is slowed.
- *Dimensions.*—Height after 7 years: 0.8 m–1.0 m. Width (spread) after 7 years: 0.8 m–1.0 m.
- *Hardiness.*—Survives in USDA Zone 7; grown in USDA Zones 7–9.
- *Root system.*—Fibrous.
- *Propagation.*—Propagation is accomplished by tissue culture or by semi hardwood to hardwood cuttings.
- *Time to develop roots.*—From 6 to 8 weeks to initiate roots.
- *Temperature for rooting.*—Rooting occurs when rooting medium is maintained within temperature range 16° C. to 28° C.
- *Crop time.*—An established plant in a 1 gallon container takes from two to three years to produce from a rooting cutting.
- *Disease and pest susceptibility.*—The species *Ilex vomitoria* is native to the Southeastern U.S., and has relatively no disease or pest susceptibility. 'CAROLINA RUBY' is neither less nor more susceptible to pests or diseases than the species or in comparison to other cultivars of the species known to the inventor.

Trunk:
- *Trunk shape.*—Cylindrical.
- *Main trunk dimensions.*—7 cm–10 cm in diameter and 0.8 m–1.0 m in height.
- *Trunk surface.*—Smooth.
- *Trunk color.*—197B.
- *Lenticels.*—Present.
- *Lenticel dimensions.*—2 mm–3 mm in length, 2 mm–3 mm in width.
- *Lenticel shape and aspect.*—Narrow, horizontal.
- *Lenticel color.*—197A.

Branches:
- *Branching.*—Dense, well-branched. Branches spaced 0.7 cm to 2 cm apart.
- *Branch arrangement.*—Alternately whorled around main branch, with interval of 2.5 cm to 6 cm between each whorled cluster.
- *Branch shape.*—Cylindrical.
- *Branch surface.*—Glabrous.
- *Branch angle at emergence.*—90 degrees.
- *Dimensions of branch (early season growth).*—6 cm–11 cm in length, 2 cm–4 cm in diameter.
- *Dimensions of branch (late season growth).*—2 cm–6 cm in length, 2 cm–4 cm in diameter.
- *Branch color.*—197B.
- *Internode distance.*—2 mm–5 mm.
- *Lenticels.*—Present.
- *Lenticel dimensions.*—Less than 1 mm in length and width.
- *Lenticel shape.*—Hemispherical.
- *Lenticel color.*—197A.

Foliage:
- *Type.*—Evergreen: leaves persist for two years.
- *Arrangement.*—Alternately whorled.
- *Leaf shape.*—Elliptical.
- *Leaf margins.*—Serrate.
- *Division.*—Simple.
- *Apex.*—Obtuse.
- *Base.*—Cuneate.
- *Leaf surfaces (abaxial and adaxial).*—Smooth, glabrous.

*Leaf dimensions.*—1.2 cm–2.5 cm in length and 0.6 cm to 1 cm in width.
*Leaf color* (*adaxial surface*).—139A.
*Leaf color* (*abaxial surface*).—137C.
*Venation pattern.*—Pinnate.
*Vein color* (*abaxial and adaxial surface*).—As leaves.
*Attachment.*—Petiolate.
*Petiole color.*—58A.
*Petiole surface.*—Very light pubescent.
*Petiole dimensions.*—2 mm–5 mm length and 1 mm. in width.
*Stipules.*—Absent.
*Fragrance.*—None.

Flowers:
*Sexuality.*—Only pistillate flowers present.
*Type.*—Tetramerous (4-merous): flower parts (petals, sepals, stamens or staminodia) appear as sets of 4.
*Arrangement.*—Clusters in axils and clusters distributed along stems and shoots of previous year's growth.
*Attachment.*—Pedicels of each individual flower in a cluster meet at stem: no peduncle.
*Pedicels.*—1.5 mm–4 mm in length, approximately 0.5 mm in diameter, smooth, color 137C.
*Flowers per branch.*—Very numerous: in excess of 100.
*Flower shape.*—Rotate, shallow bowl.
*Flower persistent or self-cleaning.*—Self-cleaning.
*Flower diameter.*—5 mm–8 mm.
*Flower depth.*—4 mm.
*Petal number.*—4 per flower.
*Petal color* (*both surfaces*).—White.
*Petal surface.*—Glabrous, puberulent.
*Petal length.*—2 mm–3.5 mm.
*Petal width.*—1 mm–2 mm.
*Petal shape.*—Oblong elliptic.
*Petal apex.*—Rounded.
*Petal base.*—Truncate.
*Fused or unfused.*—Fused at the base.
*Petal margin.*—Entire.
*Bud.*—Shape: Ovoid. Color (sepals): 137A. Dimensions (just prior to opening): 2.5 mm in length and 1.5 mm in diameter.
*Calyx.*—Dimensions: 4 mm in depth and 5 mm in diameter. Surface: Glabrous.
*Sepals.*—4 in number. Shape: Broadly ovate to rounded. Color (both surfaces): 137C. Dimensions: Length: 2 mm–3 mm, width: 2 mm. Apex: Rounded. Base: Truncate. Margins: Entire.
*Fragrance.*—None.

Reproductive organs:
*Stamens.*—Absent (flower is pistillate).
*Pollen.*—Absent.
*Staminodia.*—4, approximately 2 mm–3 mm in length, white, translucent with non-functioning anthers white or very pale yellow.
*Ovary.*—Shape: Conic-ovoid. Dimensions: 3 mm in height, 2.5 mm in diameter. Color: 144A.
*Stigma.*—Capitate, 1 mm in depth and diameter, color yellow-green, N144C.
*Fruit.*—Type: Drupe containing 4 striated nutlets. Shape: Globose, 6 mm–8 mm in diameter, with depression at detachment of stigma. Color: Immature 144A, mature glossy, bright red 44A.

It is claimed:

1. A new and distinct cultivar of *Ilex* plant named 'CAROLINA RUBY' as described and illustrated herein.

* * * * *